US009510733B2

(12) United States Patent
Yen et al.

(10) Patent No.: US 9,510,733 B2
(45) Date of Patent: Dec. 6, 2016

(54) ENDOSCOPE AND A METHOD FOR CHEMICAL MODIFICATION OF THE MEMBERS THEREOF

(71) Applicant: NATIONAL TAIWAN UNIVERSITY, Taipei (TW)

(72) Inventors: Men-Luh Yen, Taipei (TW); Tai-Horng Young, Taipei (TW); Hsu-Hsien Chang, Taipei (TW); Yu-Shin Wang, Taipei (TW)

(73) Assignee: NATIONAL TAIWAN UNIVERSITY, Taipei (TW)

( * ) Notice: Subject to any disclaimer, the term of this patent is extended or adjusted under 35 U.S.C. 154(b) by 116 days.

(21) Appl. No.: 14/084,811

(22) Filed: Nov. 20, 2013

(65) Prior Publication Data

US 2014/0371528 A1  Dec. 18, 2014

(30) Foreign Application Priority Data

Jun. 17, 2013 (TW) .............................. 102121438 A (51) Int. Cl.
| | |
|---|---|
| *A61B 1/04* | (2006.01) |
| *A61B 1/00* | (2006.01) |
| *A61B 1/12* | (2006.01) |
| *G02B 27/00* | (2006.01) |
| *G02B 23/24* | (2006.01) |

(52) U.S. Cl.
CPC ............ *A61B 1/00142* (2013.01); *A61B 1/126* (2013.01); *A61B 1/127* (2013.01); *G02B 23/2476* (2013.01); *G02B 27/0006* (2013.01); *A61B 1/0011* (2013.01)

(58) Field of Classification Search
USPC ........ 600/104, 109, 114, 121–125, 153–159, 600/139, 141, 146; 427/2.12; 604/95.04, 604/528
See application file for complete search history.

(56) References Cited

U.S. PATENT DOCUMENTS

| | | | | | |
|---|---|---|---|---|---|
| 5,993,380 | A | * | 11/1999 | Yabe | A61B 1/00142 600/121 |
| 6,004,263 | A | * | 12/1999 | Nakaichi | A61B 1/00165 600/120 |
| D583,266 | S | * | 12/2008 | Wong | D10/78 |
| 2005/0085692 | A1 | * | 4/2005 | Kiehn | A61B 1/00105 600/130 |
| 2006/0089533 | A1 | * | 4/2006 | Ziegler | A61B 1/00156 600/114 |
| 2010/0174144 | A1 | * | 7/2010 | Hsu | A61B 1/00087 600/122 |
| 2012/0041268 | A1 | * | 2/2012 | Grey | A61B 1/00105 600/199 |
| 2012/0178995 | A1 | * | 7/2012 | Newton, IV | A61B 1/00101 600/121 |

* cited by examiner

*Primary Examiner* — Timothy J Neal
(74) *Attorney, Agent, or Firm* — Chun-Ming Shih (57) ABSTRACT

An endoscope and a method for chemical modification of the members thereof are provided, on one hand, a transparent isolation film is utilized such that the tissue fluid inside a subject cannot stick to a lens of the endoscope to maintain the optimal image capturing status of the lens of the endoscope without the need to extract the endoscope frequently from the body of the subject, such that not only the time consumed in the examination process may be reduced, but also the uncomfortable feeling of the subject in the examination process may be decreased; on the other hand, a chemical modification method for members of the endoscope is provided to reduce the negative impact on the lens of the endoscope resulted from liquid pollutant or mist, moisture.

8 Claims, 7 Drawing Sheets

Hydrophilic Compound: lysine    Hydrophilic Compound: diamine

ENDOSCOPE AND A METHOD FOR CHEMICAL MODIFICATION OF THE MEMBERS THEREOF

CROSS-REFERENCE TO RELATED APPLICATIONS

This application claims the priority of Republic of China Patent Application No. 102121438 filed on Jun. 17, 2013, in the Intellectual Property Office Ministry of Economic Affairs Republic of China, the disclosure of which is incorporated herein by reference.

BACKGROUND OF THE INVENTION

1. Field of the Invention

The invention relates to an endoscope and a chemical modification method for the members thereof. More specifically, it is an endoscope and a chemical modification method of the members thereof capable of reducing impacts on image capturing from lens of the endoscope due to liquid pollutant or mist, moisture.

2. Descriptions of the Related Art

With the advancement of medical technology, various medical devices for clinical examination have been developed and used widely to facilitate medical personnel to diagnose illness state accurately for diagnosis of ulcer or tumor existence with respect to organs such as stomach, esophagus, intestinal canal, trachea etc. The endoscope examination is the most common item among various clinical examination items. The endoscope examination is one of invasive examination for observation of organs inside human body. In an endoscope examination process, at first, a lens of an endoscope has to pass through the body cavity of a subject into the interior of the human body, and images of organs inside the body of the subject are extracted through the lens by the optical image capturing device of the endoscope, followed by the extracted image information is transmitted through an information transmission medium, such as optical fiber, to the exterior for display and for observation and diagnosis.

As an endoscope enters inside the body of a subject, it is very difficult to avoid contact with blood or biological tissues (referred to as pollutant hereinafter) inside the body of the subject, such that the lens of the endoscope is polluted very easily, and thereby, the effect of image extraction through the lens by the optical image capturing device is impacted, and even more, error diagnosis made by medical personnel may occur with respect to the illness state of the subject. Generally speaking, as medical personnel are performing an endoscope examination, once the lens is polluted, the lens has to be withdrawn out from the body of the subject for cleaning for the acquisition of the clearest image. However, the subject will feel uncomfortable in the process of lens withdrawal and insertion. Therefore, the withdrawal process of the endoscope lens has to be performed slowly, such that the examination time will get longer and the subject will suffer from more pain.

To this, the announced Taiwan issued patent No. M418659 proposes a tissue expander, which expands a tissue inside the body of a subject to prevent the lens surface of the endoscope from adhesion by tissue fluid such that the usability state of the endoscope is maintained. As a result, frequent withdrawal of endoscope, when used, from the body of the subject is no more necessary. However, tissue expansion with such a method may injure soft and fragile organs of the subject once careless, so that most medical personnel do not accept such method. In addition, both U.S.A. patent applications No. 2003130674A1 and No. 20090264703 propose an endoscope cleaning device, which installs additionally a structure similar to a brush outside the lens surface of the endoscope, such that the brush is allowed to scrape pollutants to-and-fro on the lens surface once the lens surface is adhesive of pollutants. However, the lens surface will inevitably be scraped as the brush is scraping the pollutants, such that the lens of the endoscope has to be replaced frequently. The expense for the replacement of the lens of the endoscope is not small.

From above, those skilled in the art are eager to figure out the problem about how to provide an endoscope that is capable of reducing the time consumed by endoscope examination, reducing uncomfortable feeling of the subject induced by the endoscope examination, and increasing the service life of the endoscope.

SUMMARY OF THE INVENTION

In view of various problems with respect to previous technologies mentioned above, one of the main purposes of the invention is to provide an endoscope and a chemical modification method for the members thereof to reduce the necessary time for an endoscope examination, reduce pain of a subject induced in the endoscope examination, and increase the service life of lens by decreasing the opportunity with respect to adhesion of pollutants onto lens for the endoscope.

To achieve the object mentioned above and other objects, the invention proposes an endoscope, inclusive of an endoscope body, a transparent isolation film accessory, a hollow outer tube and a handle. The endoscope body is comprised of a lens, an image transmission module and a lighting module. The lens is used to capture images, the image transmission module is used to transmit image information acquired by the lens, and the lighting module is used to provide illumination for image capturing of the lens. The transparent isolation film accessory may be arranged in the endoscope in a detachability manner, and have a film offering wheel and a film collection wheel. The film offering wheel may provide a clean transparent isolation film for the lens surface of the lens for the clean transparent isolation film to cover the lens surface of the lens such that the lens surface is protected from contact with pollutants. The hollow outer tube is provided with a head opening and a tail opening at head and tail ends thereof, respectively. The tail opening is for the endoscope body to go through, such that the endoscope body enters the internal space of the hollow outer tube. The head opening exposes the transparent isolation film covering the lens surface of the lens for the lens to capture images smoothly through the transparent isolation film. The handle is arranged at the tail end of the endoscope body to join the hollow outer tube at the tail opening side of the hollow outer tube. An outer wall of the handle is extended with an actuator owned additionally by the transparent isolation film accessory to apply a force for the film offering wheel to rotate, such that a clean transparent isolation film is provided for the lens, and simultaneously, the polluted transparent isolation film on the lens moves toward the film collection wheel for the film collection wheel to collect the polluted transparent isolation film.

Compared to conventional technologies, the endoscope of the invention has a transparent isolation film used to separate pollutants from the lens, and thus reduce the opportunity of adhesion of pollutants onto the lens. Therefore, the time consumed in examination process may be reduced, the uncomfortable feeling of the subject induced in the examination process may be reduced and the service life of the lens may be increased.

BRIEF DESCRIPTION OF THE DRAWINGS

The above and other aspects, features and other advantages of the present invention will be more clearly understood from the following detailed description taken in conjunction with the accompanying drawings, in which.

DETAILED DESCRIPTION OF THE PREFERRED EMBODIMENT

Embodiments of the present invention will now be described in detail with reference to the accompanying drawings. The invention may, however, be embodied in many different forms and should not be construed as being limited to the embodiments set forth herein. Rather, these embodiments are provided so that this disclosure will be thorough and complete, and will fully convey the scope of the invention to those skilled in the art. In the drawings, the shapes and dimensions of elements may be exaggerated for clarity, and the same reference numerals will be used throughout to designate the same or like components.

The invention provides an endoscope, which may reduce the pollution degree of a lens of the endoscope due to tissue fluid inside the body of a subject in a chemical or physical manner, and has effects of self-cleaning and adhesion reduction for mist and moisture. Thus, frequent withdrawal of the endoscope from the body of the subject is unnecessary in an examination process to reduce the time consumed by the endoscope examination effectively, and reduce the uncomfortable feeling of the subject induced in the endoscope examination.

Figure 4:
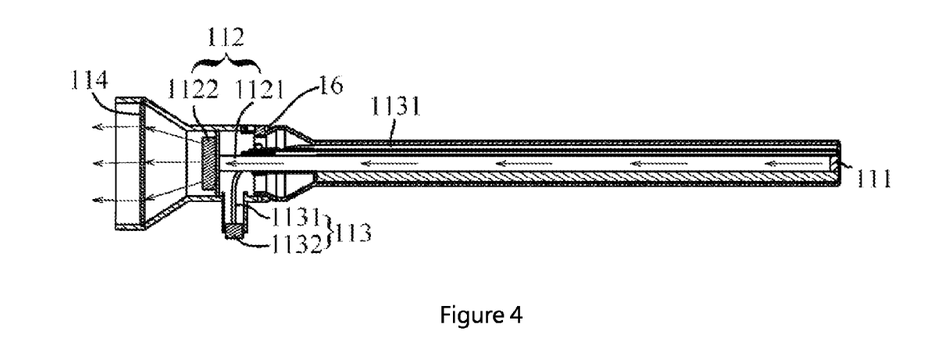
FIG. 4 is a sectional view showing the endoscope illustrated in FIG. 1.
Figure 5:
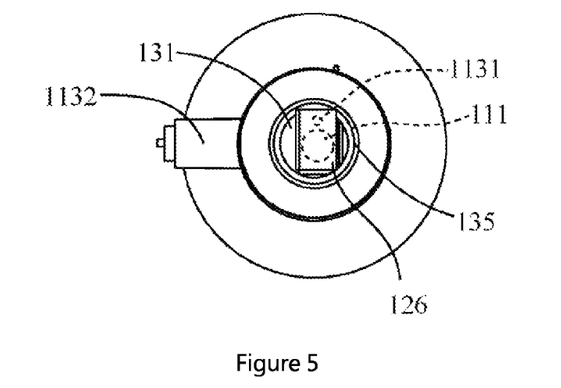
FIG. 5 is a front view showing the endoscope illustrated in FIG. 1.
Figure 14:
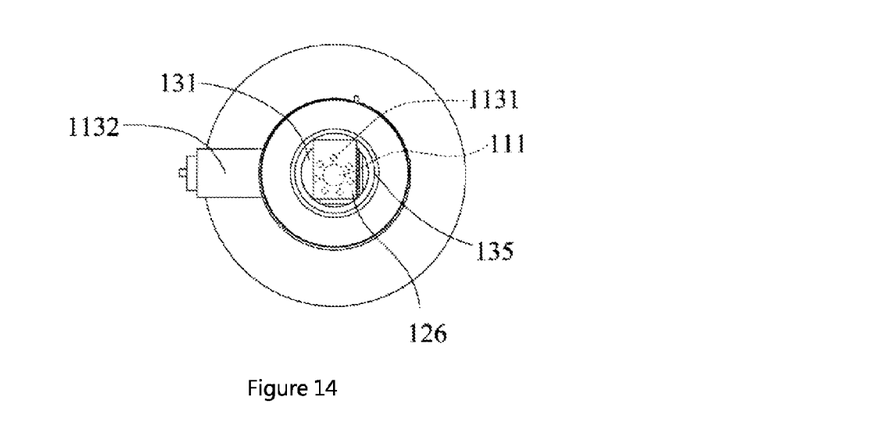
FIG. 14 is a schematic view showing an arrangement of multiple optical fibers surrounding a lens of an endoscope according to the invention.
Figure 15:
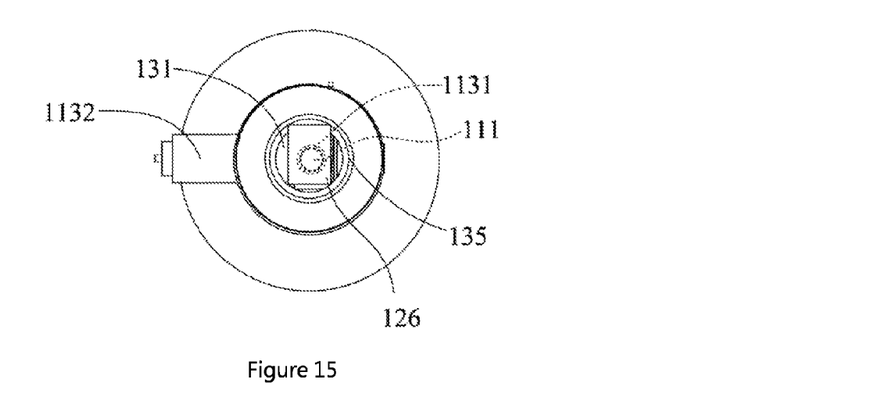
FIG. 15 is a schematic view showing an arrangement of one single optical fiber surrounding a lens of an endoscope according to the invention.
Figure 16:
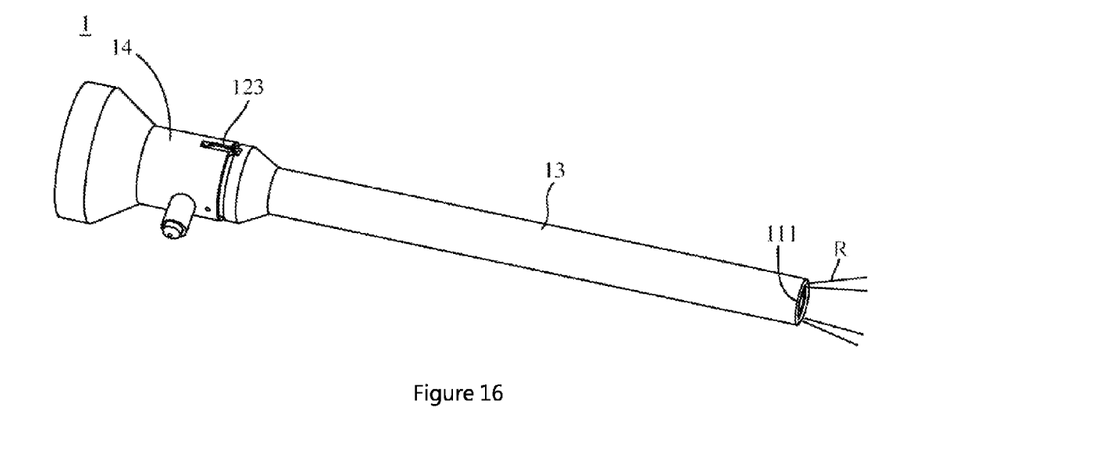
FIG. 16 is a schematic view showing that optical fibers of a lighting module provide lighting around an image capturing area of a lens according to the invention.

Refer to FIGS. 1 to 5, which are schematic view of the endoscope according to the invention. As shown in these figures, an endoscope 1 mainly includes an endoscope body 11, a transparent isolation film accessory 12, a hollow outer tube 13 and a handle 14. As shown in FIG. 4, the endoscope body 11 has a lens 111, an image transmission module 112 and a lighting module 113. The lens 111 is used for image capturing. The lighting module 113 is composed of at least one light transmission optical fiber 1131 and a light source 1132. Light from the light source 1132 may be guided to a lighting portion by the light transmission optical fiber 1131 to provide lighting for an image capturing area in the lens 111. The aforementioned lighting module 113 may be provided with at least one optical fiber 1131 surrounding a lens surface of the lens 111, refer to FIGS. 14 and 15, respectively, for the optical fiber 1131 to provide lighting around the image capturing area in the lens 111, as shown in FIG. 16, symbol R indicates a light emitted by the optical fiber 1131 for providing lighting such that image capturing effect of the lens 111 may be optimized. The image transmission module 112 is used to deliver image information acquired by the lens 111. The image transmission module 112 may be composed at least of an image information transmission optical fiber 1121 and an optical lens set 1122. The image information transmission optical fiber 1121 may be used to deliver optical image information, while the optical lens set 1122 may be used to image the optical image information delivered by the optical fiber 1121 onto an eyepiece 114 of the endoscope body 11 for medical personnel to observe the status inside the body of the subject through the eyepiece 114.

Figure 10:
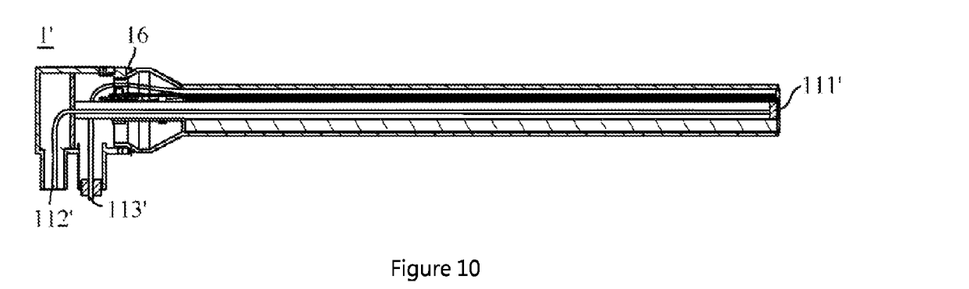
FIG. 10 is a sectional view showing another embodiment of an endoscope according to the invention.
Figure 11:
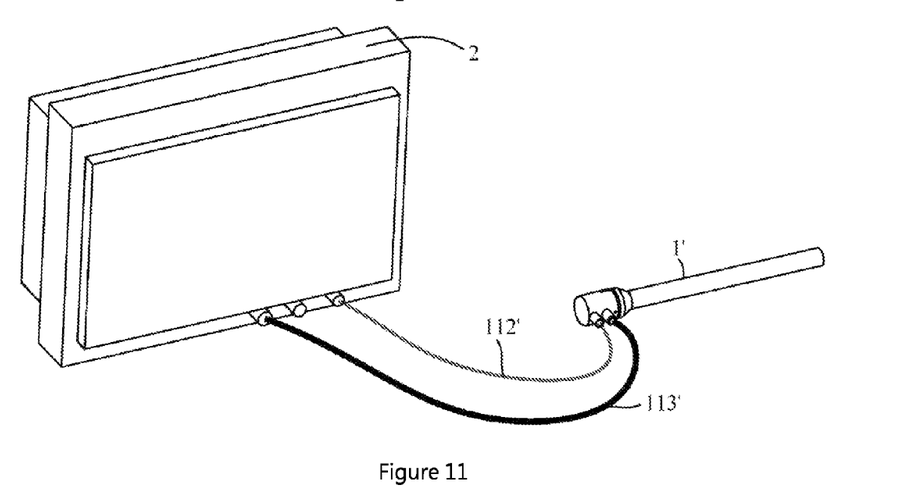
FIG. 11 is a schematic view showing a using state of an endoscope according to the invention.

Additionally, FIG. 4 uses arrows to show a method of delivery of the optical image information acquired by the lens 111 to the eyepiece 114 in this embodiment, but the invention is not limited thereto. Further refer to FIGS. 10 and 11, which show another embodiment of an endoscope according to the invention. As shown in the FIGS. 10 and 11, a lens 111' of the endoscope 1' may be a charged coupled device (CCD), such that the arrangement of eyepiece is no more necessary, and image information may be transmitted to a monitor 2 external to the endoscope through an image transmission module 112' for several medical personnel to view the status inside the body of the subject through the monitor 2 at the same time. A lighting module 113' is used to provide illumination for image capturing of the lens 111'.

Figure 1:
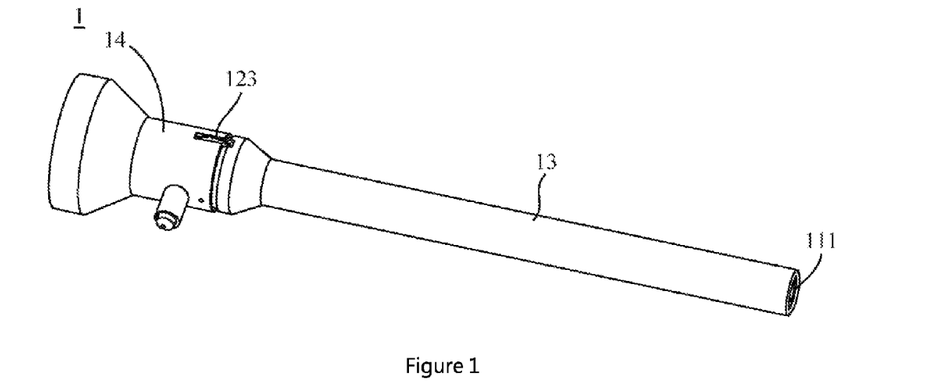
FIG. 1 is a stereogram view showing one embodiment of an endoscope according to the invention.
Figure 2:
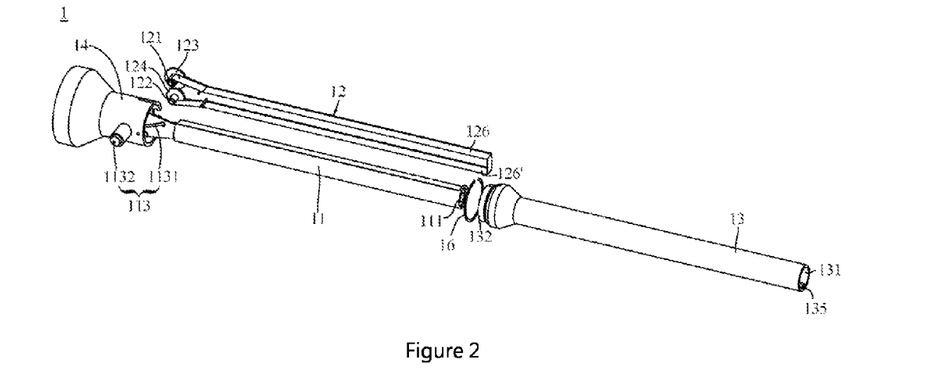
FIG. 2 is an exploded view showing the endoscope illustrated in FIG. 1.
Figure 3:
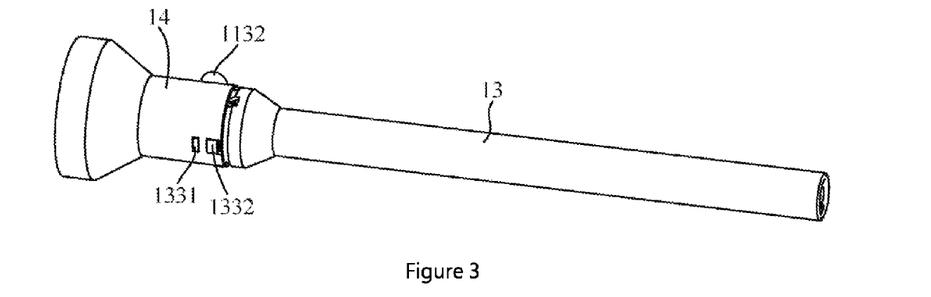
FIG. 3 is a stereogram view showing the endoscope illustrated in FIG. 1 from another view angle.

As shown in FIG. 2, the transparent isolation film accessory 12 is arranged on the endoscope body 11 in a detachment method. The transparent isolation film accessory 12 has a film offering wheel 121 and a film collection wheel 122. The film offering wheel 121 may keep on providing clean transparent isolation film 126 for a lens surface of the lens 111 for the lens surface of the lens 111 to be covered with a clean transparent isolation film 126. Such that pollutants are kept from contact with the lens 111 by the transparent isolation film 126, the service life of the lens 111 is further increased, and the image capturing effect of the lens 111 is optimized. Additionally, the transparent isolation film 126 may also cover the illumination surface of the optical fiber 1131 to keep pollutants from polluting the illumination surface, while the lens 111 has the optimal image capturing illumination effect. The film collection wheel 122 may collect polluted transparent isolation film 126' on the lens surface of lens 111.

Figure 8:
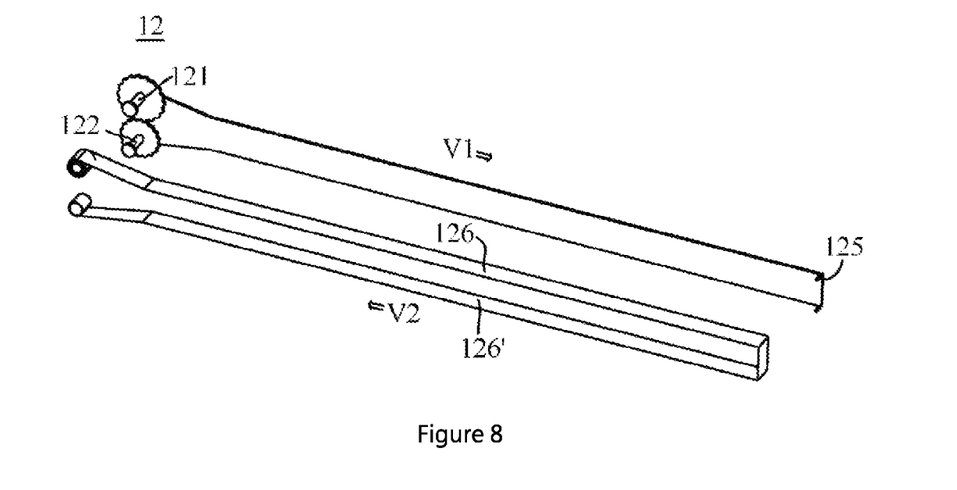
FIG. 8 is an exploded view of a transparent isolation film accessory of an endoscope according to the invention.

It is noted that, the diameter of the lens surface of the lens of the endoscope may be designed to be 5 mm or 10 mm or other sizes. A 10 mm-sized lens surface has the advantage of large visual field, so that image capturing maybe still possible as partial area on the lens surface is polluted, but the 10 mm-sized lens surface leaves larger wound for the body of the subject in comparison to a 5 mm-sized lens surface. In the contrary, the 5 mm-sized lens surface has the advantage of leaving smaller wound for the body of the subject, but the 5 mm-sized lens surface might have to be withdrawn from the body of the subject for wiping once polluted because of smaller visual field, and the process is troublesome. In the invention, the transparent isolation film of the endoscope may cover the lens surface with size of 5 mm or 10 mm or other sizes to keep pollutants from contact with the lens surface. Further refer to FIG. 8, which is an exploded view showing a transparent isolation film accessory in the embodiment. As shown in FIG. 8, The transparent isolation film accessory 12 may further have a guiding portion 125, which provides guidance for the clean transparent isolation film 126 on the film offering wheel 121 to move toward the lens surface of the lens 111, the moving direction of the transparent isolation film 126 is as shown by V1 arrows in FIG. 8, or for the polluted transparent isolation film 126' on the lens surface of the lens 111 to move toward the film collection wheel 122, the moving direction of the transparent isolation film 126' is as shown by V2 arrows in FIG. 8. The transparent isolation films above may be made of material that is transparent but not harmful to human body (for example, not cause anaphylaxis to human body). The material to be chosen may be polyethylene, polypropylene, PVC (polyvinyl chloride), PET (polyethylene terephthalate), polyurethane, thermoplastic polyurethane resin, polycarbonate, polystyrene, polymethyl methacrylate, or polylactic acid.

Moreover, it is noted that the film offering wheel and the film collection wheel are arranged in separation with a space formed in a middle portion therebetween. The image transmission module or the lighting module may go through the space, such that the assembly process of the transparent isolation film accessory in the endoscope body will not be impacted by the interference of the image transmission module or the lighting module.

For the hollow outer tube, as shown in FIG. 2, the hollow outer tube 13 is formed with a head opening 131 and a tail opening 132 on head and tail ends, respectively. The tail opening 132 is for the endoscope body 11 to go through such that the endoscope body 11 enters the interior space of the hollow outer tube 13, and the head opening 131 exposes the transparent isolation film 126 covering the lens surface of the lens 111 for the lens 111 to extract images smoothly through the transparent isolation film 126, refer to FIG. 5. To reduce pollutants introduced into the film collection wheel 122 by the transparent isolation film 126', the tube wall of the hollow outer tube 13 may be further provided with a scraping portion 135 to scrape partial pollutants on the surface of the transparent isolation film 126'.

The handle 14 is set at the tail end of the endoscope body 11, and is joined with the hollow outer tube 13 on the tail opening 132 side of the hollow outer tube 13. The outer wall of the handle 14 is provided with a slot to extend an actuator 123 of the transparent isolation film accessory 12. The actuator 123 may apply a force thereto to drive rotation of the film offering wheel 121 to provide the clean transparent isolation film 126 for the lens surface of the lens 111, and provide simultaneously a force for the polluted transparent isolation film 126' on the lens surface of the lens 11 to move toward the film collection wheel 122 such that the polluted transparent isolation film 126' is collected by the film collection wheel 122. In one embodiment of the invention, the actuator 123 is a gear wheel joined the film offering wheel 121, while the film collection wheel 122 is joined with a follower 124 having follower relationship with the actuator 123. Thus, the film collection wheel 122 may rote simultaneously with the rotation of the film offering wheel 121 to collect the polluted transparent isolation film 126'.

Figure 9:
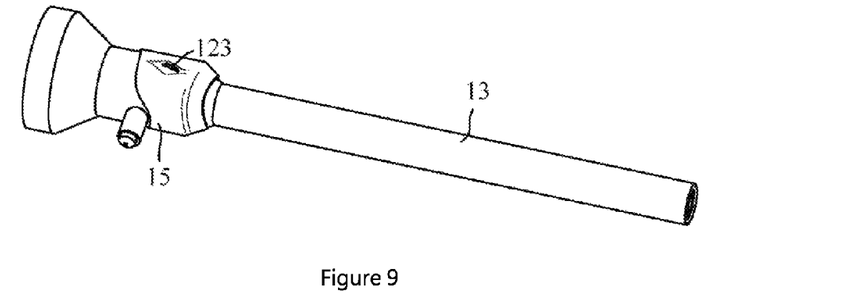
FIG. 9 is a schematic view showing a handle of an endoscope covered with a soft waterproof film according to the invention.

Further refer to FIG. 9, the outer wall of the handle 14 of the endoscope 1 may further be sheathed with a soft waterproof film 15 to keep water from entering the interior space from, for example, the slot of the handle 14 for the internal elements inside the endoscope body 11 to be damaged. Also, medical personnel may also apply a force to the actuator 123 through the soft waterproof film 15 to control the rotation of the film offering wheel 121. Similarly, a washer 16 may also be set circumferentially at the joint of the handle 14 and the hollow outer tube 13 to reduce the opportunity of the entrance of water into the interior space of the handle 14 and the hollow outer tube 13.

As medical personnel operate the endoscope 1 of the invention, the traveling direction of the endoscope body 11 may be controlled by only holding the handle 14 for the lens 111 of the endoscope body 11 to capture images at appropriate position inside the body of the subject. At the same time, the actuator 123 may be driven to rotate by the thumb of medical personnel to provide the clean transparent isolation film 126 for the lens surface of the lens 111, while maintaining the lens 111 in an image capture status. As a result, no frequent withdraw from the body of the subject due to polluted lens surface when the endoscope is under use to reduce the time consumed for the endoscope examination effectively, and reduce the inappropriate painful feeling induced by frequent access of the endoscope to the body of the subject as the subject is in the endoscope examination.

Figure 6:
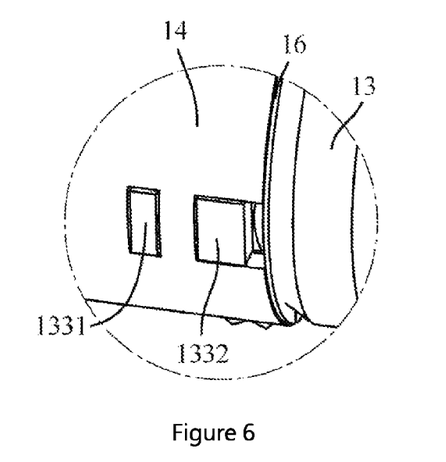
FIG. 6 is an enlarged view showing area A in the endoscope illustrated in FIG. 3, which is a joining state diagram of a hollow outer tube and a handle of the endoscope according to the invention.
Figure 7:
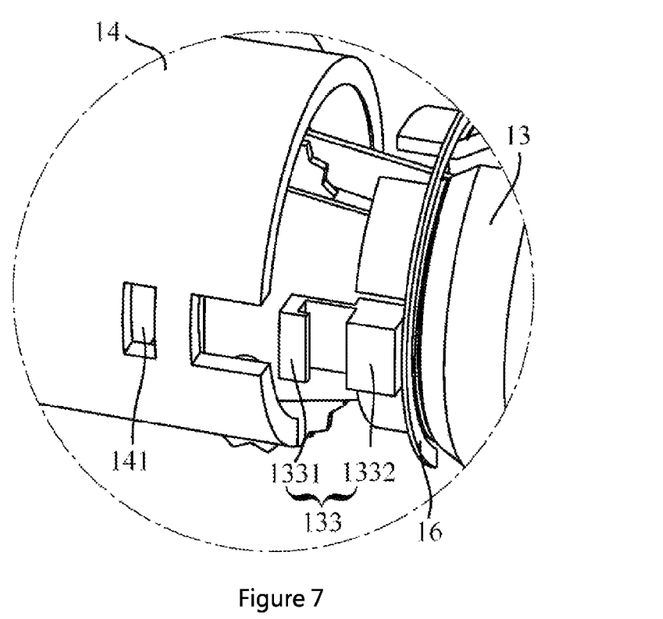
FIG. 7 is an enlarged view of the area A in the endoscope illustrated in FIG. 3, which is a detachment state diagram for the hollow outer tube and the handle of the endoscope according to the invention.

In one embodiment of the invention, refer to FIGS. 6 and 7, a hook 1331 of a cantilever 133 is formed at the joint of the hollow outer tube 13 and the handle 14. Correspondingly, a joining hole 141 is formed on the handle 14 at a position corresponding to the hook 1331. The joining hole 141 is for accommodating the hook 1331 to constrain the freedom of the hook 1331 by the hole wall of the joining hole 141, while to maintain a joining state of the handle 14 and the hollow outer tube 13, as shown in FIG. 6. Besides, there is also a pressing portion 1332 at the end opposite to the hook 1331 on the cantilever 133 of the hollow outer tube 13 for pressing to apply a force to the cantilever 133 for the hook 1331 to leave the joining hole 141. At the same time, the handle 14 and the hollow outer tube 13 may be separated, and the transparent isolation film accessory 12 may be extracted from the endoscope body 11 for replacing.

In other words, after the endoscope completes the examination for the subject, partial transparent isolation film in the transparent isolation film accessory has been polluted by tissue fluid inside the body of the subject. Medical personnel using the endoscope of the invention may press the pressing portion to replace the transparent isolation film accessory fitted in the endoscope body to keep the polluted transparent isolation film accessory from impacting the health of the next subject. It should be noted that, the structure of above cantilever and joining hole may also be formed at the handle 14 and the hollow outer tube 13, but the invention is not limited thereto.

The higher the hydrophilicity of the glass lens surface of the endoscope is, the smaller the contact angle between the glass lens surface and the liquid pollutant attached thereto is. At the same time, the liquid pollutant stuck onto the glass lens surface will be dispersed uniformly to reduce negative impact for image capturing by lens. To decrease the growth of bacteria, the temperature in an operating room usually maintains very low, so that the temperature of the glass lens surface will usually far lower than the body temperature of the subject, such that normal use of the endoscope will be impacted because adhesion of mist and moisture occurs easily as the glass lens surface of the endoscope enters the body of the subject. To this, the invention provides a chemical modification method for endoscope members to increase the hydrophilicity of the glass lens surface of the endoscope body, and keep the lens surface from impact of pollution, mist and moisture.

The chemical modification method under description may comprise about the following steps: at first, immersing the glass lens surface of the endoscope body in hydrochloric acid/hydrogen peroxide for about 10 to 15 minutes, then, using a large amount of deionized water for washing, followed by immersing the glass lens surface in sodium hydroxide for about 45 minutes, and later, using deionized water for cleaning and drying, to remove the organic substances on the glass lens surface that will impact the chemical modification. After that, glass fiber and toluene are put in a 500 ml four-hole reaction bottle, and argon (Ar) is used to push out moisture in the air for about 1 hour in advance to remove oxygen and moisture on the glass lens surface that will impact the chemical modification.

Figure 17:
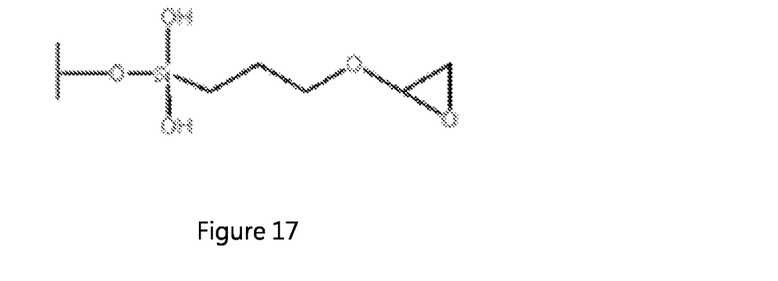
FIG. 17 is a chemical structure of chemical formula 1.

Subsequently, the glass lens surface and 3-glycidoxypropyltrimethoxysilane are placed in a toluene solution recycle system for reaction under a temperature condition from 50° C. to 120° C. by 24 hours to generate a chemical structure of chemical formula 1 as shown in FIG. 17.

Figure 18:
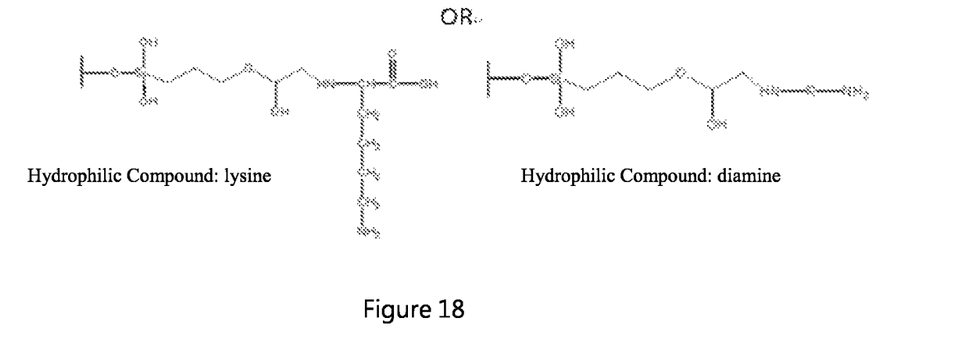
FIG. 18 is a chemical structure of chemical formula 2.

At last, the glass lens surface, after the reaction via above steps, is cleaned and dried with acetone, and is placed in hydrophilic compound solution for reaction under a temperature condition between 25° C. and 100° C. by 24 hours to form a hydrophilic chemical structure, which is shown in chemical formula 2 in FIG. 18.

Similarly, the transparent isolation film of the endoscope may be modified with the following procedures to improve the hydrophilicity of the transparent isolation film such that the transparent isolation film is kept from the impact of pollution, mist and moisture. The method of chemical modification under use is roughly stated as below: at first, the transparent isolation film is placed in carbinol to remove impurities on the surface of the isolation film, taken out for drying, the transparent isolation is placed on a panning substrate, placed in a plasma reactor with oxygen removal via vacuum process, followed by being replenished with argon, starting the plasma reactor for the surface of the transparent isolation film to generate radical, taking out the transparent isolation film from the plasma reactor after the reaction is complete, and exposing the transparent isolation film to air for radical on the surface of the transparent isolation film to be converted into peroxyl radical and alcohol group.

Next, the reacted transparent isolation film is placed in a 3-glycidoxypropyltrimethoxysilane hydrolytic condensed alcohol system for reaction. After that, the transparent isolation film after reaction with above steps is cleaned and dried to be placed in hydrophilic compound solution for chemical modification with reaction under a temperature condition between 25° C. and 100° C.

Lysine, tween, span, glycerol, amino acid, diamine compound may be chosen as above hydrophilic compound to further enhance the hydrophilicity of the glass lens surface or the transparent isolation film.

Figure 12:
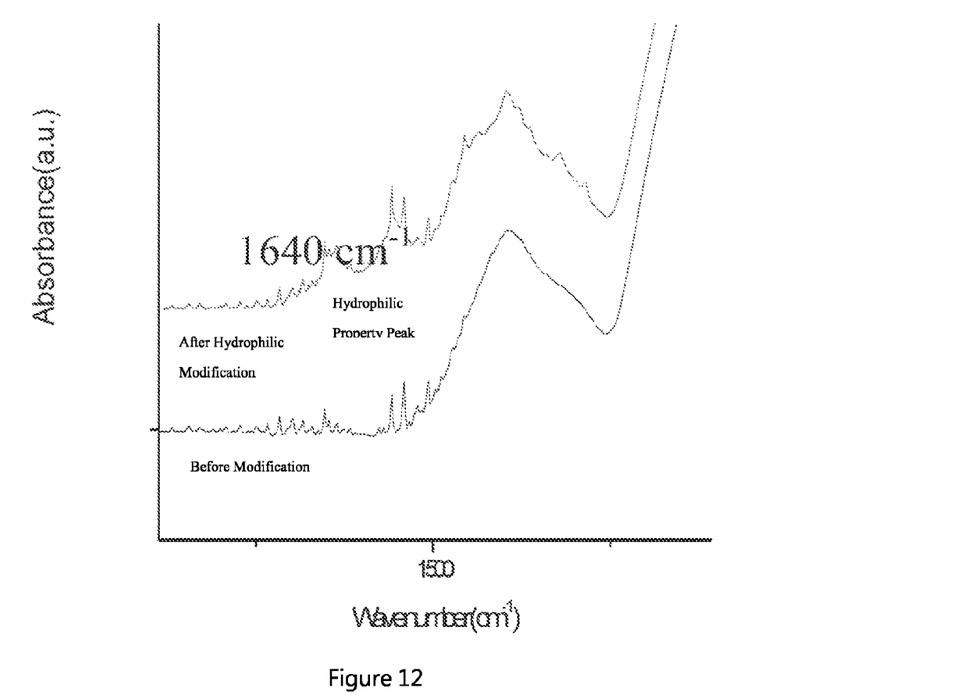
FIGS. 12 to 13 are FT-IR graphs showing a glass lens of an endoscope before and after chemical modification according to the invention, respectively.
Figure 13:
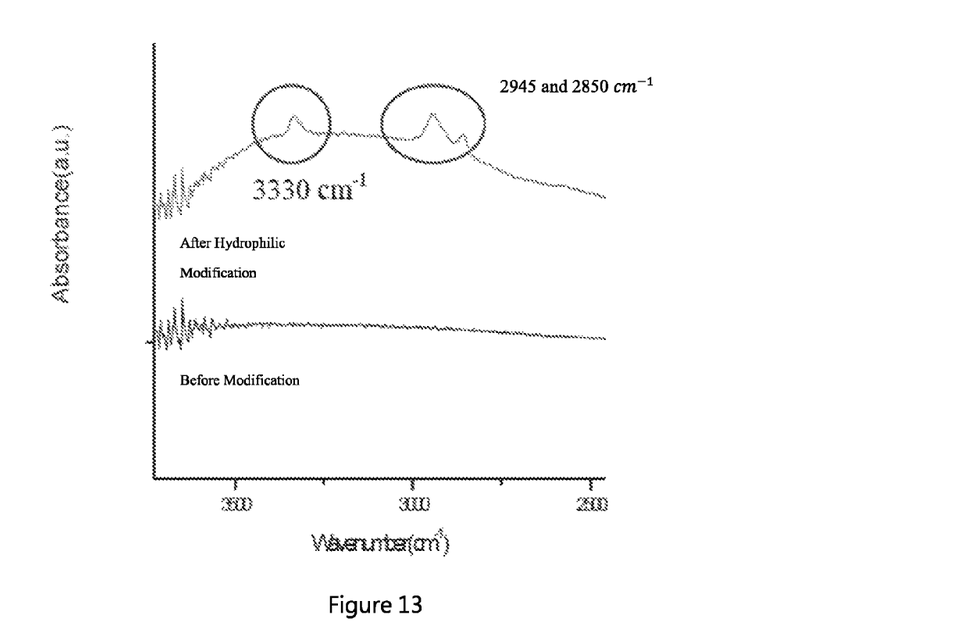

Refer to FIGS. 12 and 13 now, which show FT-IR graphs of the glass lens surface of the endoscope before and after chemical modification according to the invention. From the figures, the hydrophicility property peak of hexamethylenediamine for the glass lens surface after chemical modification is obviously higher than that before chemical modification.

Besides, the invention further provides a chemical modification method for endoscope members to improve the hydrophobicity on the glass lens surface of the endoscope body for liquid pollutants and mist, moisture not easy to be attached onto the glass lens surface. The chemical modification method of hydrophobicity may include roughly the following steps: in step 1, the glass lens surface of the endoscope body is immersed in hydrochloric acid/hydrogen peroxide and sodium hydroxide for cleaning organic residuals, respectively; and in step 2, the above glass lens surface and hydrophobic compound are placed in hydrolytic condensed alcohol water system for chemical modification with reaction under a temperature condition between 10° C. and 120° C.

Similarly, the chemical modification for the transparent isolation film of the endoscope may also be performed with the following steps to improve the hydrophobicity of the transparent isolation film. The chemical modification method under use is roughly as below: at first, the transparent isolation film is placed in carbinol to remove impurities on the surface of the isolation film, taken out for drying, the transparent isolation is placed on a panning substrate, placed in a plasma reactor with oxygen removal via vacuum process, followed by being replenished with argon, starting the plasma reactor for the surface of the transparent isolation film to generate radical, taking out the transparent isolation film from the plasma reactor after the reaction is complete, and exposing the transparent isolation film to air for radical on the surface of the transparent isolation film to be converted into peroxyl radical and alcohol group. Subsequently, the transparent isolation film and hydrophobic compound are placed in a hydrolytic condensed alcohol water system for reaction under a temperature condition between 10° C. and 120° C.

Figure 19:
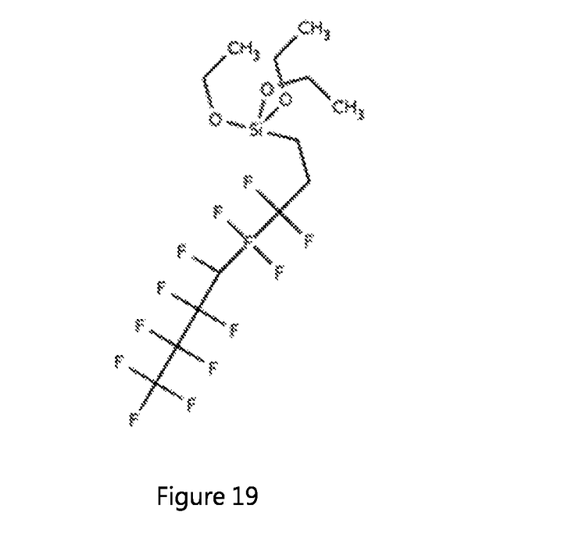
FIG. 19 is a chemical structure of chemical formula 3.

The above hydrophobic compound is a compound of 13-fluorine siloxane, 15-fluorine siloxane, 17-fluorine siloxane, or 8-carbon to 20-carbon siloxane, wherein the chemical formula of 13-fluorine siloxane is as shown in FIG. 19.

In summary, the endoscope and the chemical modification method of the members thereof provided by the invention have at least the following technical features:

1. The transparent isolation film is used to separate the lens surface of the lens from pollutants inside the body of the subject to keep the lens surface of the lens from direct pollution.

2. The detachability is designed for the used transparent isolation film accessory to be taken out for replacement easily from the endoscope for guarantee of medical safety.

3. The actuator is extended from the outer wall of the handle of the endoscope in order for medical personnel to force and drive the film offering wheel to rotate to provide the clean transparent isolation film for the lens surface, and move away the polluted transparent isolation film on the lens surface.

4. The chemical modification may be performed for the glass lens surface or the transparent isolation film to improve hydrophilicity such that the liquid pollutants stuck on the glass lens surface and the transparent isolation film are dispersed uniformly to reduce the negative impact of the stuck liquid pollutants on the image capturing by the lens.

5. The chemical modification may be performed for the glass lens surface or the transparent isolation film to improve hydrophobicity such that liquid pollutants cannot stick onto the glass lens surface and the transparent isolation film easily to reduce the negative impact of the stuck liquid pollutants on the image capturing by the lens. Besides, the glass lens surface and the transparent isolation film after chemical modification may also reduce adhesion of moisture and mist.

What is claimed is:

1. An endoscope, including:
    an endoscope body, having a lens, an image transmission module and a lighting module, said lens with lens surface being used to capture image, said image transmission module being used to transmit image information acquired by said lens, and said lighting module being used to provide illumination for image capturing of said lens;
    a transparent isolation film accessory, being provided in said endoscope body in a detachable manner, said transparent isolation film accessory having a film offering wheel and a film collection wheel, said film offering wheel may provide a clean transparent isolation film for the lens surface of said lens for said clean transparent isolation film to cover the lens surface of said lens, and further keep pollutants from contact with the lens surface of said lens;
    a hollow outer tube, having a head opening and a tail opening, said tail opening being for said endoscope body to go through to enter an interior space of said hollow outer tube; said head opening being externally exposed the transparent isolation film, covering the lens surface of said lens, for said lens to capture images by said transparent isolation film; and
    a handle, being arranged at the tail end of said endoscope body, being joined with said hollow outer tube on the tail opening side of said hollow outer tube, an outer wall of said handle being protruded with an actuator coaxially attached to the film offering wheel, the actuator being able to apply a force to drive said film offering wheel to rotate to provide the aforementioned clean transparent isolation film for the lens surface of said lens, while a polluted transparent isolation film on the lens surface of said lens being moved forward to said film collection wheel by a follower coaxially attached to the film collection wheel and engaging with the actuator in order to collect said polluted transparent isolation film by said film collection wheel,
    wherein the actuator and the follower are gears, and the follower is directly engaged and driven by the actuator;
    wherein a soft waterproof film further covers the outer wall of said handle and the actuator;
    wherein, said hollow outer tube is formed with a cantilever with a hook at a joint of said handle and the hollow outer tube, a position of said handle corresponding to said hook is formed with a joining hole, said joining hole is provided for accommodating said hook for maintaining the joining of said handle and said hollow outer tube by a hole wall of said joining hole, and
    wherein, the cantilever of said hollow outer tube further has a pressing portion protruded at one end opposite to said hook; when the pressing portion is pushed down, the hook of the cantilever disengages from the joining hole.

2. The endoscope as claim 1, wherein, said lighting module has a lighting portion, and said transparent isolation film also covers said lighting portion and exposes outside said head opening for said lighting module to provide illumination for image capturing by said lens through said transparent isolation film.

3. The endoscope as claim 1, wherein, said transparent isolation film is polyethylene, polypropylene, polyvinyl chloride, polyethylene terephthalate, polyurethane, thermoplastic polyurethane resin, polycarbonate, polystyrene, polymethyl methacrylate, or polylactic acid.

4. The endoscope as claim 1, wherein, said transparent isolation film accessory is formed with a guiding portion to provide guidance for the transparent isolation film of said film offering wheel to move toward the lens surface of said lens, or for the polluted transparent isolation film on the lens surface of said lens to move forward said film collection wheel.

5. The endoscope as claim 4, wherein, the tube wall of said hollow outer tube is further provided with a scraping portion to scrape partial pollutants on said transparent isolation film.

6. The endoscope as claim 1, further including a washer set circumferentially at the joint of said handle and said hollow outer tube.

7. The endoscope as claim 1, wherein, said film offering wheel and said film collection wheel are arranged to be separated with a space formed for going through said endoscope body.

8. The endoscope as claim 1, wherein, said image transmission module is composed at least of an image information transmission optical fiber and an optical lens set; said lighting module is composed at least of a light transmission optical fiber and a light source.

* * * * *